United States Patent [19]
Kamen

[11] Patent Number: 5,988,167
[45] Date of Patent: Nov. 23, 1999

[54] FOAM CUFF FOR LARYNGEAL MASK AIRWAY

[76] Inventor: Jack M. Kamen, 8782 N. Cricket Tree La., Indianapolis, Ind. 46260

[21] Appl. No.: 08/850,414

[22] Filed: May 2, 1997

[51] Int. Cl.$^6$ .................................................. A61M 16/00
[52] U.S. Cl. ................................ 128/207.15; 128/207.14
[58] Field of Search ...................... 128/207.15, 200.26, 128/207.14, 912; 604/96

[56] References Cited

U.S. PATENT DOCUMENTS

| | | |
|---|---|---|
| 2,548,602 | 4/1951 | Greenburg . |
| 3,640,282 | 2/1972 | Kamen et al. ...................... 128/207.15 |
| 3,799,173 | 3/1974 | Kamen ................................ 128/207.15 |
| 3,889,685 | 6/1975 | Miller, Jr. et al. ......................... 604/96 |
| 3,971,385 | 7/1976 | Corbett ..................................... 604/96 |
| 4,509,514 | 4/1985 | Brain .................................. 128/207.15 |
| 4,995,388 | 2/1991 | Brain .................................. 128/207.15 |
| 5,009,639 | 4/1991 | Keymling .................................. 604/96 |
| 5,038,766 | 8/1991 | Parker ................................ 128/200.26 |
| 5,042,469 | 8/1991 | Augustine ........................... 128/200.26 |
| 5,203,320 | 4/1993 | Augustine ........................... 128/207.14 |
| 5,241,956 | 9/1993 | Brain .................................. 128/207.15 |
| 5,249,571 | 10/1993 | Brain .................................. 128/207.14 |
| 5,297,547 | 3/1994 | Brain .................................. 128/207.15 |
| 5,305,743 | 4/1994 | Brain .................................. 128/207.15 |
| 5,308,325 | 5/1994 | Quinn et al. ............................... 604/96 |
| 5,339,805 | 8/1994 | Parker ................................ 128/200.26 |
| 5,355,879 | 10/1994 | Brain .................................. 128/207.15 |
| 5,391,248 | 2/1995 | Brain ........................................ 156/242 |
| 5,439,444 | 8/1995 | Andersen et al. ......................... 604/96 |
| 5,477,851 | 12/1995 | Callaghan et al. ................. 128/207.15 |
| 5,513,627 | 5/1996 | Flam .................................. 128/200.26 |
| 5,632,271 | 5/1997 | Brain .................................. 128/207.15 |
| 5,653,690 | 8/1997 | Booth et al. ............................... 604/96 |

FOREIGN PATENT DOCUMENTS

| | | |
|---|---|---|
| 0 294 200 A2 | 12/1988 | European Pat. Off. . |
| 0 294 200 B1 | 12/1988 | European Pat. Off. . |
| 0 448 878 A2 | 10/1991 | European Pat. Off. . |
| 2 267 034 | 11/1993 | United Kingdom . |
| 922073 | 2/1996 | United Kingdom . |
| PCT/GB95/01292 | 12/1995 | WIPO . |
| PCT/GB96/02425 | 4/1997 | WIPO . |

OTHER PUBLICATIONS

Instruction Video —Intavent Laryngeal Mask Airway.
Instruction Manual —The Intavent Laryngeal Mask, Oct. 1992.
Instruction Manual —LMA Laryngeal Mask Airway, Aug. 1996.
Brochure —LMA Laryngeal Mask Airway.

*Primary Examiner*—Aaron J. Lewis
*Attorney, Agent, or Firm*—Barnes & Thornburg

[57] ABSTRACT

An artificial airway is provided for permitting medical personnel access to a patient's airway. The artificial airway includes a foam cuff laryngeal mask having an air tube, a pilot tube, and a laryngeal mask. The air tube and the laryngeal mask cooperate to form a gas passage that permits gases to flow through the foam cuff laryngeal mask. The laryngeal mask includes a foam cuff having a pliable sheath filled with a resilient material. Air is drawn out of the resilient material through the pilot tube which causes the foam cuff to deflate. The foam cuff laryngeal mask is then inserted into the patient's airway and positioned over the larynx. Air is allowed to enter the pilot tube and the resilient material expands so that the foam cuff forms a substantial seal with the larynx.

24 Claims, 6 Drawing Sheets

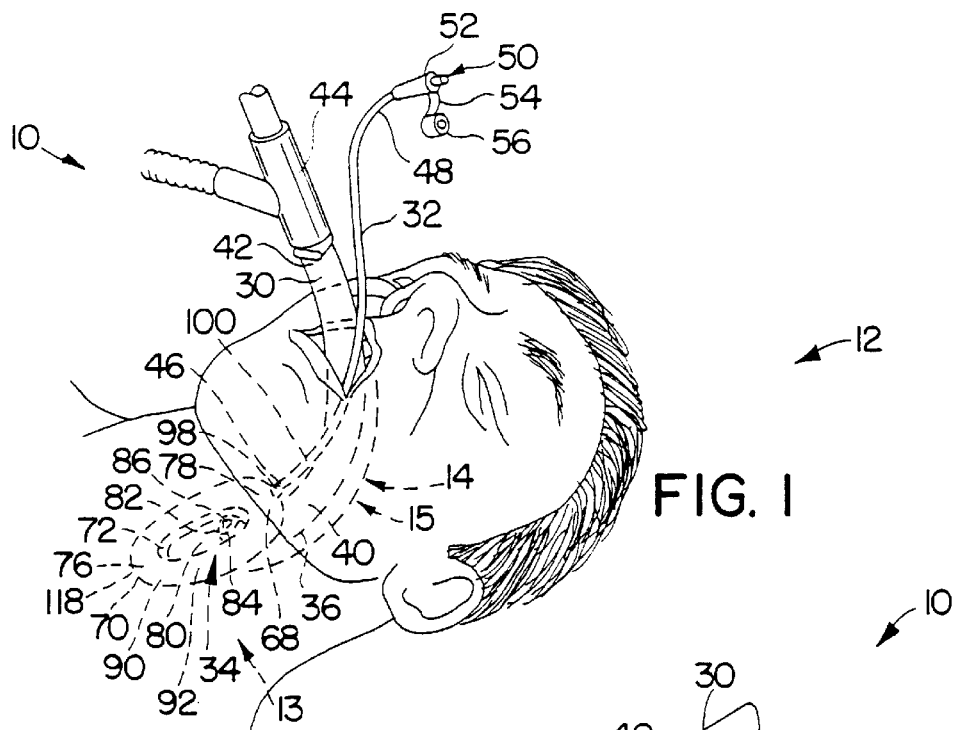
FIG. 1
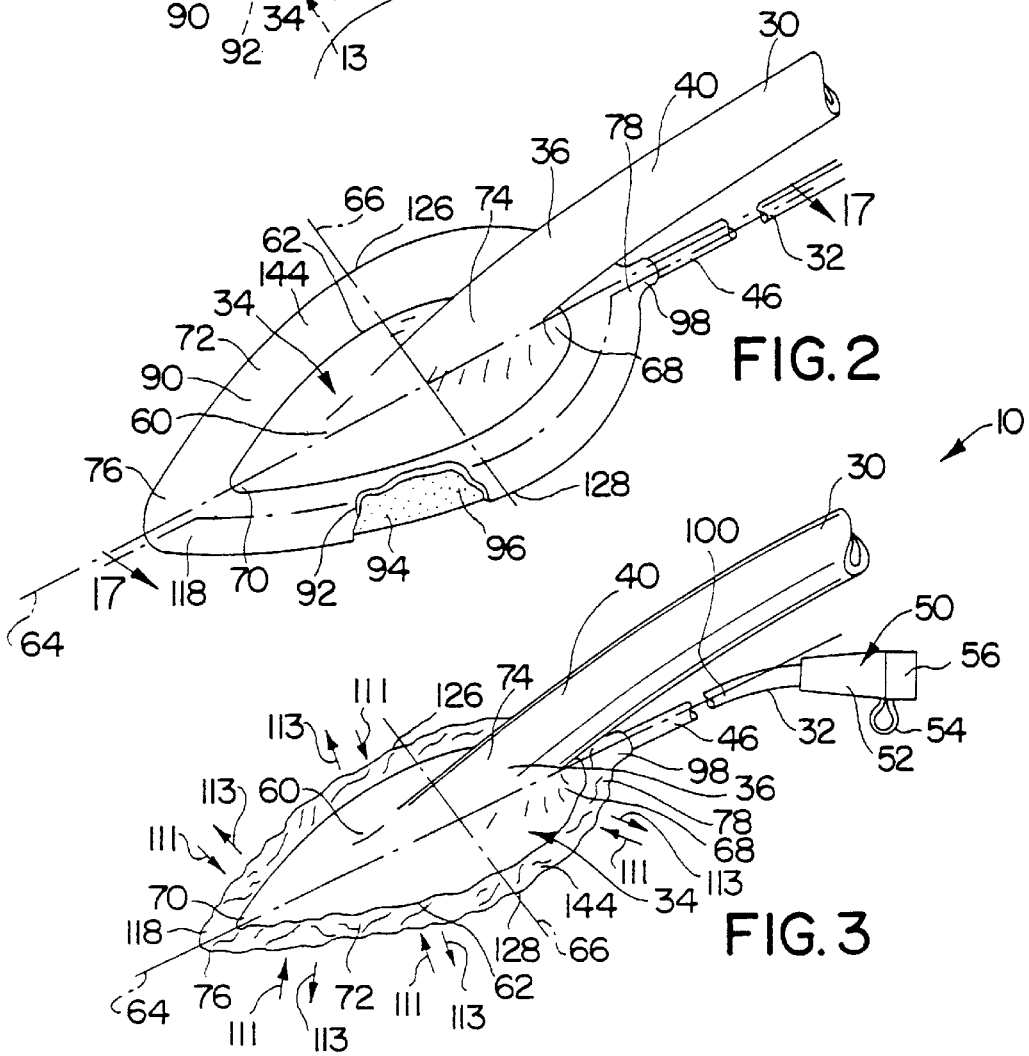
FIG. 2
FIG. 3

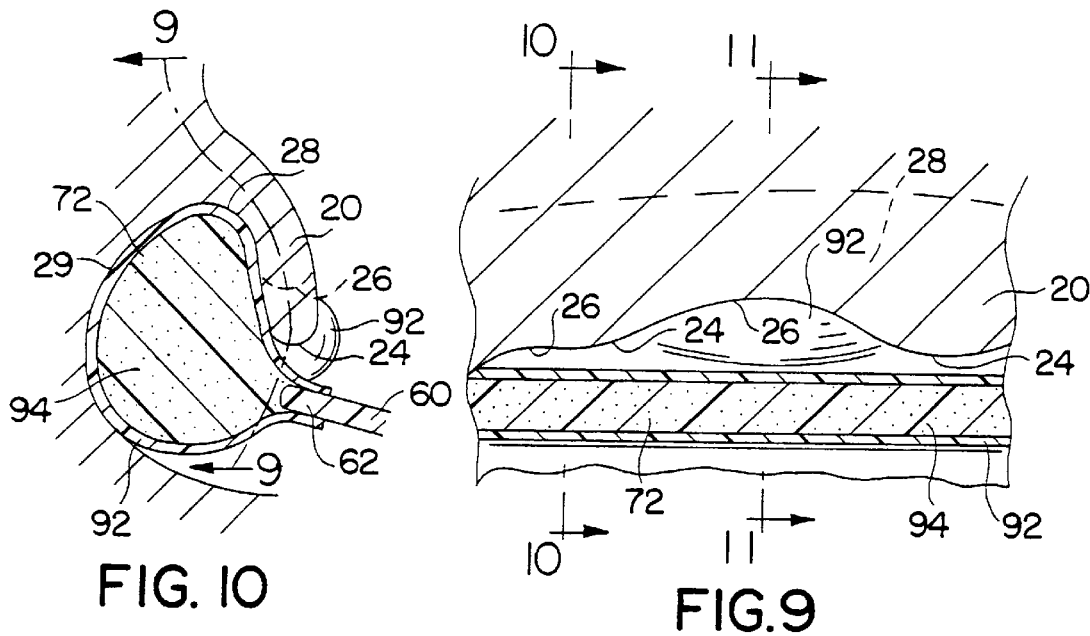
FIG. 10
FIG. 9
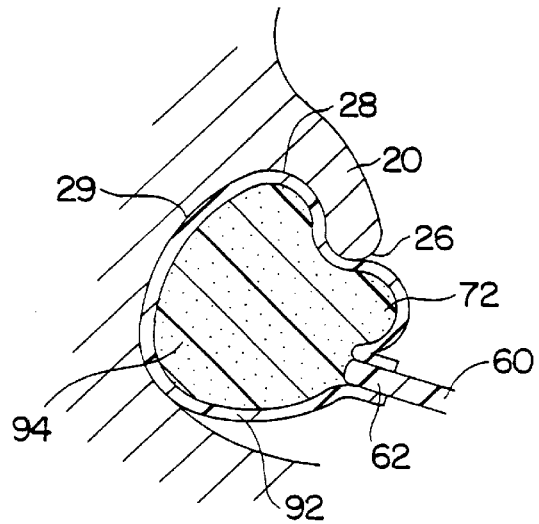
FIG. 11

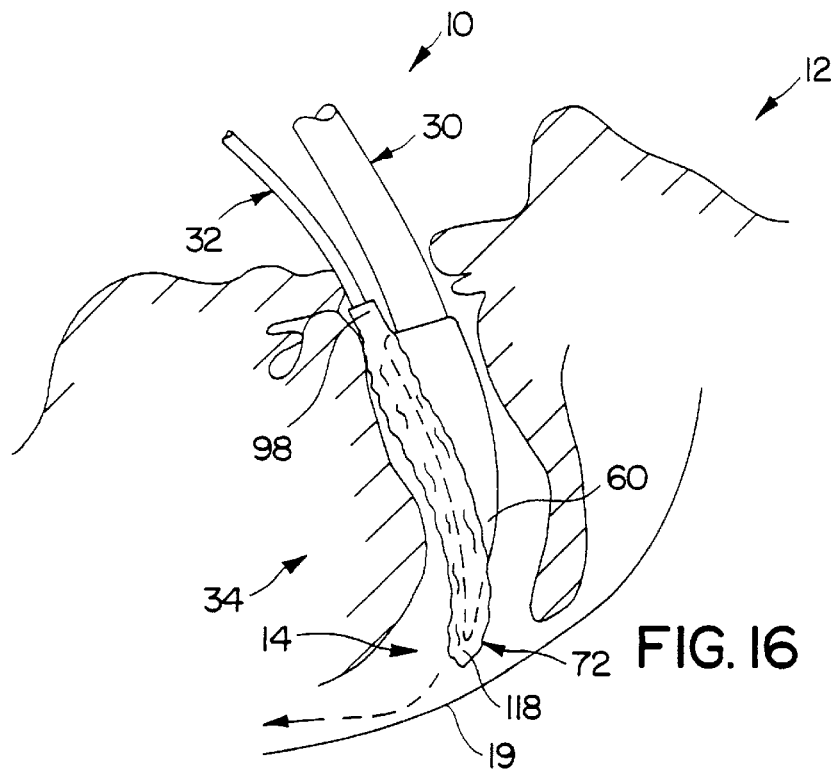
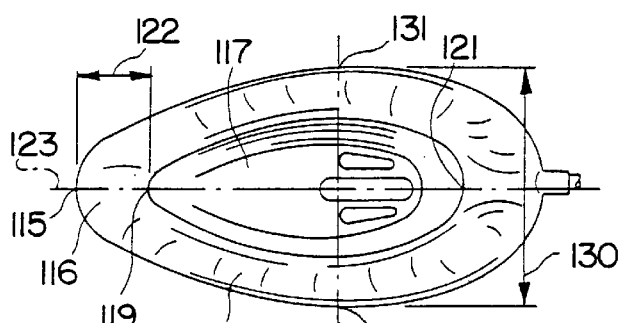
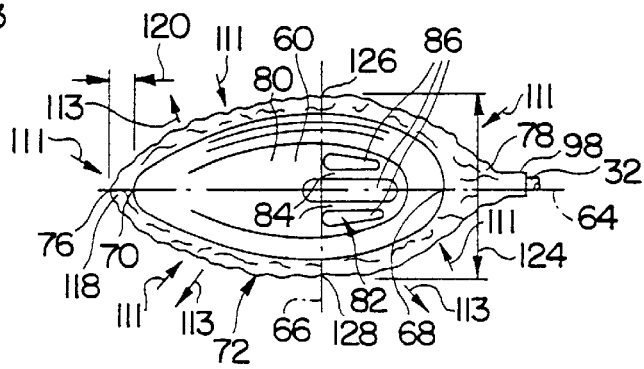

FOAM CUFF FOR LARYNGEAL MASK AIRWAY

BACKGROUND AND SUMMARY OF THE INVENTION

The present invention relates to artificial airways that medical personnel use for patient airway access. More particularly, the present invention relates to laryngeal mask airways that incorporate a cuff filled with a resilient foam-like material to effectively seal the connection between the artificial airway and the patient's airway.

Medical personnel use artificial airways for airway management in an effort to monitor and control gas flow to and from the patient's lungs. This includes gases used in the administration of anesthesia. Artificial airways can be connected to the patient's airway in various locations and with various mechanisms. The most common artificial airways consist of endotracheal catheters that are inserted through the larynx and into the patient's trachea. See, for example, U.S. Pat. Nos. 3,640,282 to Kamen et al. and 3,799,173, to Kamen. Other artificial airways are laryngeal masks positioned over the laryngeal opening. See, for example, U.S. Pat. Nos. 4,509,514 and 5,355,879 to Brain.

Conventional laryngeal masks provide a seal over the laryngeal opening by using a cushion or inflatable ring cuff that is inflated with air. This inflation process consumes valuable medical personnel time that could be dedicated to other functions beneficial to the patient. Furthermore, a cushion inflated in such a manner may create excessive pressure on the laryngeal rim resulting in tissue damage. A laryngeal mask that reduces the possibility of exerting excessive pressure on the airway tissue caused by excessive cuff inflation would be a welcome improvement in laryngeal masks.

Furthermore, when deflated, conventional inflatable ring cuffs are flexible and include a frontal portion or tip. The flexible nature of the frontal portion of the ring cuff may cause it to fold back during insertion of the conventional laryngeal mask into the patient's airway. This would prevent the inflatable ring cuff from forming an effective seal over the laryngeal opening. The conventional laryngeal mask airway must then be removed, re-prepared for insertion, and then reinserted. The patient would, in all probability, not breath and may not be ventilated during this interval. This could result in possible harm to the patient secondary to hypoxia. A cuff that effectively seals over the laryngeal opening, but has a frontal tip that is less likely to fold back would save valuable medical personnel time and be a useful advancement in laryngeal masks.

According to the present invention, a laryngeal mask airway is provided for use in patients having an airway and a larynx. The larynx has a laryngeal opening and a laryngeal rim surrounding the laryngeal opening.

The laryngeal mask airway of the present invention includes a catheter or air tube for the passage of gases, a pilot tube, and a laryngeal mask. The catheter includes a proximal end and a mask end spaced apart from the proximal end. The pilot tube includes a port end and a flow control end spaced apart from the port end. The laryngeal mask is attached to the mask end of the catheter. The laryngeal mask includes a back plate having an outer rim and a foam cuff attached to the outer rim. The port end of the pilot tube is attached to and opens into the foam cuff. The foam cuff includes a resilient material and a pliable sheath coupled to the back plate. The pliable sheath is formed to include an interior region and the resilient material is positioned to lie within the interior region. The resilient material expands and deflates between a deflated position and an expanded position to seal over the laryngeal opening.

The foam cuff is deflated by using a syringe or similar pressure-creating device to withdraw air out of the resilient material through the pilot tube. A pilot tube cap closes off the pilot tube to maintain the vacuum created in the resilient material.

Next, the laryngeal mask airway is inserted into the patient's airway and over the patient's laryngeal opening and rim. To inflate a previously deflated foam cuff, the pilot tube cap is removed and air enters the deflated resilient material through the pilot tube. The air is drawn into the foam cuff by negative pressure generated by an expansive nature of the deflated resilient material. The resilient material then expands and the foam cuff substantially forms a seal over the laryngeal opening and with the laryngeal rim.

The resilient material is yieldable and contacts and conforms to peaks and valleys that define the laryngeal rim. This contact does not create high pressure on the airway tissue that may be created by conventional inflatable ring cuffs. Thus, the foam cuff according to the present invention reduces the potential for damage to the laryngeal tissue.

According to another preferred embodiment of the present invention, the resilient material is contoured to include crests and canyons that generally follow the configuration of the tissues of the laryngeal rim. This contoured resilient material allows the cuff to reasonably match the configuration defined by the peaks and valleys of the laryngeal rim and U-shaped channels surrounding a portion of the laryngeal rim without relying exclusively on the expansive nature of the resilient material. This further reduces the potential pressures exerted on the laryngeal tissues, thus reducing tissue damage, while also creating a more effective seal.

The yieldable fit provided by the resilient material allows it to expand deeper into the valleys of the laryngeal rim and the U-shaped channels. The additional expansion into the valleys and U-shaped channels creates a locking barrier to motion perpendicular to the depth of the valleys and U-shaped channels. These barriers will increase the resistance against laryngeal mask motion in a direction perpendicular to the valleys' and U-shaped channels' depth. This resistance will increase with the additional expansion into the valleys and U-shaped channels provided by the use of contoured foam cuffs.

As mentioned previously, conventional laryngeal masks have frontal tips that have a tendency to fold back during insertion. The foam cuff tip according to the present invention, decreases in length while being deflated so that its tip length is less than that of a conventional inflatable ring cuff tip upon insertion into a patient's airway. This decreased tip length reduces the probability that the foam cuff tip will fold back during insertion when compared to the conventional inflatable ring cuff tip. An additional feature of a foam cuff is that it deflates inward. This decreases the foam cuff's width and allows for easier insertion into and through the mouth and pharynx in route to the patient's larynx.

Conventional inflatable ring cuff tips also develop a "hinging" tendency while in the deflated position that can further increase the likelihood of fold back if the cuff tip strikes the pharyngeal wall during insertion. A deflated foam cuff tip according to the present invention has less of a tendency to hinge back because its rigidity increases with deflation. Therefore, the decreased length and increased rigidity of the foam cuff tip reduces the likelihood that the tip will fold back upon engaging the patient's airway during insertion.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a patient showing a laryngeal mask airway inserted into the patient's airway for providing a passageway for gases entering and exiting the patient's lungs (not shown), the artificial laryngeal mask airway includes a catheter, a foam cuff laryngeal mask (in phantom) connected to the catheter, and a pilot tube connected to the foam cuff, the pilot tube including a pilot tube cap;

FIG. 2 is a perspective view of the foam cuff laryngeal mask, with portions cut away, showing the foam cuff laryngeal mask including a foam cuff having a resilient material and a pliable sheath covering the resilient material, the foam cuff and the resilient material being in an expanded position at ambient pressure;

FIG. 3 is a perspective view of the foam cuff laryngeal mask, similar to FIG. 2, showing the foam cuff in a deflated position due to a vacuum having been applied to the resilient material and the pilot tube cap being in a closed position to maintain the vacuum;

FIG. 9 is a sectional view taken along line 9—9 of FIG. 10 of the patient showing the laryngeal rim including peaks and valleys and the foam cuff substantially sealing the peaks and valleys;

FIG. 10 is a sectional view taken along 10—10 of FIG. 9 showing the foam cuff sealing a peak and a valley (in phantom) of the laryngeal rim;

FIG. 11 is a sectional view, similar to FIG. 10, taken along 11—11 of FIG. 9 showing the foam cuff sealing a valley of the laryngeal rim;

FIG. 12 is a bottom plan view of a conventional inflatable ring cuff of a conventional laryngeal mask airway showing the inflatable ring cuff in a deflated position;

FIG. 15 is a bottom plan view of the foam cuff according to the present invention in the deflated position showing the foam cuff including a foam cuff tip in a deflated position;

FIG. 16 is a sectional view of an upper airway of a patient showing the foam cuff according to the present invention being inserted into the airway without the deflated foam cuff tip folding back;

DETAILED DESCRIPTION OF THE DRAWINGS

Figure 4:
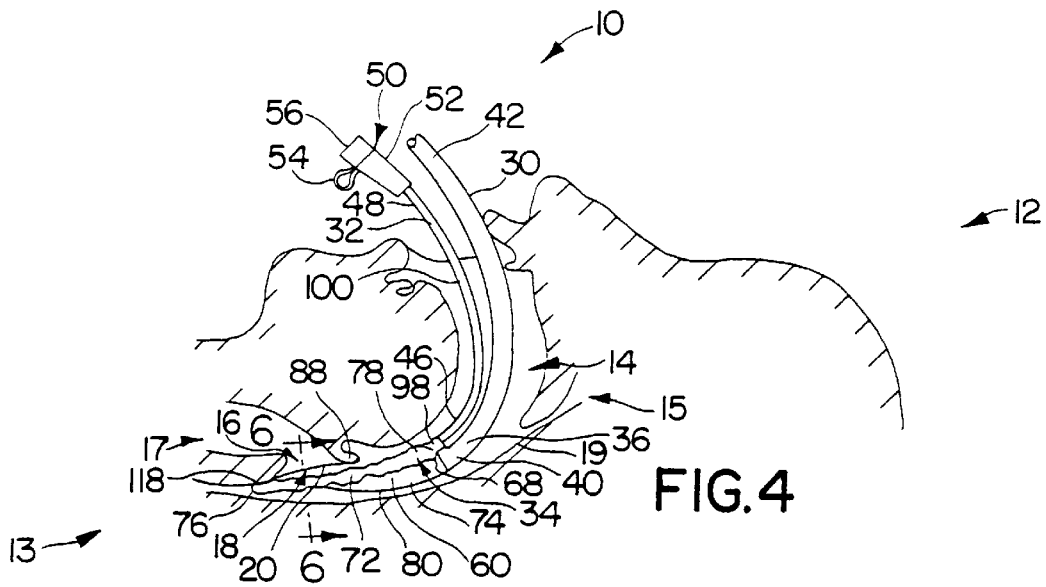
FIG. 4 is a sectional view of the patient showing the patient's airway including a laryngeal opening surrounded by a laryngeal rim and the foam cuff in a deflated position inserted into the patient's airway over the laryngeal opening.

FIGS. 1 and 4 show a foam cuff laryngeal mask airway 10 inserted into an airway 14 of a patient 12. The foam cuff laryngeal mask airway 10 includes a catheter or air tube 30, pilot tube or inflation-deflation tube 32, and laryngeal mask 34. The catheter 30 and laryngeal mask 34 are attached and cooperate to form a gas passage 36 so that gas flow entering and exiting the patient's lungs (not shown) can be controlled.

Figure 5:
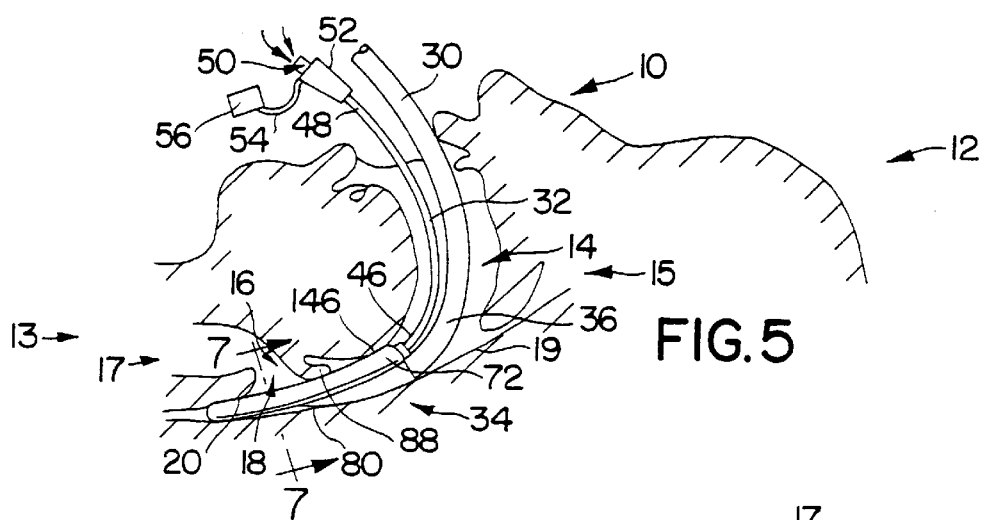
FIG. 5 is a sectional view of the patient, similar to FIG. 4, showing the foam cuff in an expanded position to substantially seal over the laryngeal opening and with the laryngeal rim.
Figure 6:
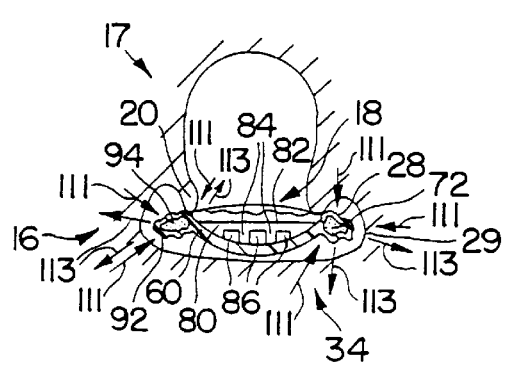
FIG. 6 is a sectional view taken along line 6—6 of FIG. 4 showing the patient's airway further including U-shaped channels surrounding a portion of the laryngeal rim and the resilient material and the foam cuff in the deflated position.
Figure 7:
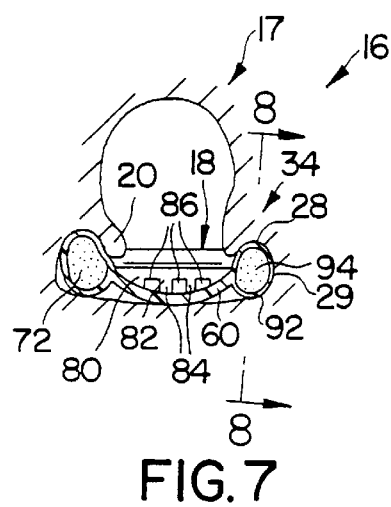
FIG. 7 is a sectional view, similar to FIG. 6, taken along line 7—7 of FIG. 5 showing the resilient material and the foam cuff in the expanded position to substantially seal over the laryngeal opening and with the laryngeal rim and U-shaped channels.

The patient's airway 14 includes a larynx 16, a laryngeal opening 18, a laryngeal rim 20 that surrounds and defines the laryngeal opening 18 as shown, for example, in FIG. 4, lateral laryngeal walls 29, and U-shaped channels 28 as shown, for example, in FIGS. 6 and 7. The U-shaped channels 28 are defined by the laryngeal rim 20 and the lateral laryngeal walls 29. The patient 12 includes a respiratory tract 13 having the larynx 16, a pharynx 15 having a posterior pharyngeal wall 19, and a trachea 17. The larynx 16 is situated between the pharynx 15 and the trachea 17. The larynx 16 is an organ of voice production and consists of a framework of cartilage and elastic membranes housing the vocal cords (not shown) and muscles (not shown) which control the position and tension of these elements. The laryngeal mask 34 engages the larynx 16 at the laryngeal rim 20 and U-shaped channels 28 to form an effective seal over the laryngeal opening 18 as shown in FIGS. 5 and 7.

The laryngeal rim 20 is defined by peaks 24 and valleys 26 as shown, for example, in FIG. 9, and is partially surrounded by the irregularly contoured U-shaped channels 28 as shown, for example, in FIGS. 6, 7, 10 and 11. The laryngeal mask 34 engages with laryngeal rim 20 and U-shaped channels 28 to seal over the laryngeal opening 18. This seal along with the gas passage 36 cooperate to allow for monitoring and adjustment and control of gas flow into and out of the patient's lungs. Such monitoring can include, but is not limited to, the measuring of gas contents and flow rates. The foam cuff laryngeal airway 10 can also be used to control the gas flow into and out of the patient's lungs in an effort to assist the patient 12 in breathing. Furthermore, the foam cuff laryngeal mask airway 10 can be used to administer inhalation of anesthetic gas mixtures to the patient 12.

The catheter 30 includes a mask end 40 attached to the laryngeal mask 34, a proximal end 42 spaced apart from the mask end 40, and a medical equipment mount 44 attached to the proximal end 42. The catheter 30 is flexible and contoured so as to follow a general curvature of the airway 14. The medical equipment mount 44 connects with an appropriate piece of medical equipment used to administer, control, and monitor the flow of gases (including anesthesia gases) into and out of the patient's lungs.

The catheter 30 also provides a convenient path for the insertion of fiber optic endoscopic instruments (not shown) used in the diagnosis and treatment of airway pathology. This can be done with little guidance and no injury to the airway 14.

The pilot tube 32 includes a port end 46, a flow control end 48 spaced apart from the port end 46, and a flow control mechanism 50 attached to the flow control end 48 as shown, for example, in FIGS. 1–3. In preferred embodiments, the pilot tube 32 is flexible. The flow control mechanism 50 is used to control the flow of air into or out of the pilot tube 32. In the present embodiment, the flow control mechanism 50 is a pilot tube cap that includes a male base 52 attached to the flow control end 48 of the pilot tube 32, a cap strap 54 attached to the male base 52, and a female cap 56 attached to the cap strap 54. The female cap 56 fits snugly over the male base 52 to form a substantially airtight seal over the flow control end 48 of the pilot tube 32. Furthermore, the male base 52 is formed to cooperate with a syringe or like pressure-creating device in an effort to create negative or positive pressure in the pilot tube 32. Valves, clamps, or any other devices that control air flow may also be used as flow control mechanisms 50.

The laryngeal mask 34 provides an effective connection between the mask end 40 of the catheter 30 and the patient's laryngeal rim 20 and U-shaped channels 28 to form the seal between the catheter 30 and laryngeal opening 18. This seal substantially prevents the escape of the gases that flow through the gas passage 36.

As shown in FIG. 2, the laryngeal mask 34 includes a back plate 60 having an outer rim 62, a longitudinal axis 64, and a latitudinal axis 66 perpendicular to the longitudinal axis 64. The back plate 60 includes a proximal end 68 and a distal end 70 spaced apart from the proximal end 68 along the longitudinal axis 64. The laryngeal mask 34 further includes a foam cuff 72 attached to and enclosing the outer rim 62 of the back plate 60.

The back plate 60 and mask end 40 of the catheter 30 cooperate to form a socket 74 as shown, for example, in FIGS. 2 and 3. The gas passage 36 passes through the socket 74 between the back plate 60 of the laryngeal mask 34 and the mask end 40 of the catheter 30. The back plate 60 provides flexible structural support for the transition between the catheter 30 and the foam cuff 72. In the illustrated embodiment, the back plate 60 and socket 74 are made of a rubber-like material that provides support, but is also compliant so that the patient's airway 14 is not damaged in the event of forceful contact with the laryngeal mask 34.

The back plate 60, outer rim 62, and foam cuff 72 are tear-shaped to match the general shape of the laryngeal rim 20. The proximal end 68 of the back plate 60 is rounded and the distal end 70 is generally pointed. The foam cuff 72 includes a front end 76 and a back end 78 spaced apart from the front end 76 along the longitudinal axis 64. The front end 76 is generally pointed and the back end 78 is rounded to conform to the shape of the back plate 60.

The back plate 60 is also formed to include a dome 80 as shown, for example, in FIGS. 1 and 4–7, that is positioned to lie over the laryngeal opening 18 as shown in FIGS. 4–7.

The dome 80 is formed to include an opening 82 located near the proximal end 68 as shown, for example, in FIG. 15. The opening 82 is aligned with the mask end 40 of the catheter 30 to allow the gas passage 36 to pass through the socket 74 and into the dome 80. Furthermore, the dome 80 includes cross members 84 spanning the opening 82 to form partitioned holes 86 therein as shown in FIGS. 6, 7, and 15. The cross members 84 prevent a patient's epiglottis 88 from blocking the opening 82 as shown, for example, in FIGS. 5–7.

As shown in FIG. 2, the foam cuff 72 is in the shape of a tubular oval that generally follows the shape of the outer rim 62 of the back plate 60. The foam cuff 72 includes a pliable sheath 92 connected to the outer rim 62 of the back plate 60 and a resilient material 94. The pliable sheath 92 is formed to include an interior region 96 and the resilient material 94 is positioned to lie within the interior region 96. The resilient material 94 expands and deflates between a deflated position, as shown in FIGS. 3, 4, 6, 15, and 16 and an expanded position, as shown in FIG. 1, 2, 5, 7–11, and 17. As the resilient material 94 expands and deflates, the foam cuff 72 moves between its expanded and deflated positions, respectively, to engage with the laryngeal rim 20 and U-shaped channels 28 and seal over the laryngeal opening 18.

The pliable sheath 92 forms a substantially airtight barrier over the resilient material 94. The substantially airtight barrier prevents air from entering or exiting through the pliable sheath 92 to the resilient material 94 when either negative or inflating pressure is applied to the resilient material 94. Inflating pressure is defined as pressure created by a positive pressure-creating device or ambient pressure when a vacuum exists in the resilient material.

Figure 8:
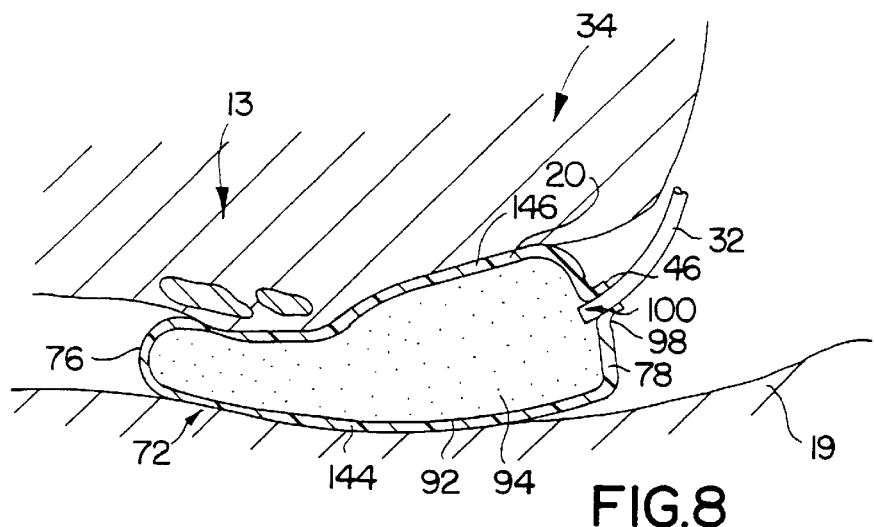
FIG. 8 is a sectional view taken along line 8—8 of FIG. 7 showing the foam cuff substantially filling a U-shaped channel.

The pliable sheath 92 is formed to include a port 98 near the back end 78 of the foam cuff 72 as shown, for example, in FIG. 8. Port end 46 of the pilot tube 32 extends into port 98 to form an air passage 100 from the resilient material 94 to the flow control end 48 of the pilot tube 32. The air passage 100 permits negative or inflating pressure applied at the flow control end 48 of the pilot tube 32 to be transferred to the resilient material 94. Likewise, the port 98 allows inflating or negative pressure applied at the port 98 to be applied within the pliable sheath 92 to the resilient material 94.

If a vacuum is applied on the flow control end 48 of the pilot tube 32, that vacuum is also transmitted to the resilient material 94. Likewise, if inflating pressure is applied to the flow control end 48, that inflating pressure is also applied to the resilient material 94.

Such vacuum or inflating pressures can be created by use of a syringe or similar pressure-creating device on the flow control mechanism 50 of the pilot tube 32. Inflating pressure can also be created by the atmosphere when negative pressure exists within the resilient material 94. If the flow control end 48 of the pilot tube 32 is sealed with a flow control mechanism 50, the air passage 100 becomes airtight. This allows the resilient material 94 to maintain its deflated or inflated position.

The resilient material 94 is a sponge-like material that is formed to include a plurality of interconnected air pockets with a pliable structure. Foamed polyurethane is one such sponge-like material. The resilient material 94 has a volume. Because the pliable sheath 92 provides a substantially airtight barrier and the resilient material 94 is pliable, the volume of the resilient material 94 is pressure sensitive. The volume increases with inflating pressure and decreases with negative pressure. Therefore, if negative pressure is applied to the resilient material 94, it contracts and if inflating pressure is applied, it expands accordingly.

When the resilient material 94 deflates, it recedes inward in direction 111 toward the outer rim 62 because the pliable sheath 92 is attached to the outer rim 62 of the back plate 60 as shown, for example, in FIG. 3. Likewise, if inflating pressure is applied to the resilient material 94, it expands away from the outer rim 62 in direction 113. Furthermore, the pliable sheath 92 is in contact with the resilient material 94 so that it recedes and expands with the resilient material 94, accordingly.

FIGS. 4 and 6 show the laryngeal mask 34 in its deflated position inserted into airway 14 positioned to lie over the laryngeal rim 20 and opening 18. To inflate laryngeal mask 34, the female cap 56 of the flow control mechanism 50 is removed from the male base 52, as shown in FIG. 5, so that air flows into the pilot tube 32 and inflates the resilient material 94 and the foam cuff 72. Inflating the resilient material 94 causes the foam cuff 72 to make contact with and seal with the laryngeal rim 20 and U-shaped channels 28, as shown in FIGS. 5 and 7–11.

The flow of air into the resilient material 94 does not require the use of a syringe or other positive pressure-creating device because ambient air pressure is sufficient to have the resilient material 94 expand to its inflated position.

The resilient material 94 expands so that foam cuff 72 of laryngeal mask 34 substantially fills in the U-shaped channels 28 as shown, for example, in FIGS. 7–11. This permits the foam cuff 72 to form an effective seal with the laryngeal rim 20 and U-shaped channels 28 and over the laryngeal opening 18.

The resilient material 94 is a yieldable sponge-like material. As shown in FIGS. 9–11, when the resilient material 94 comes into contact with a body made of higher rigidity material such as cartilage and bone, the resilient material 94 conforms more to the higher rigidity body than the higher rigidity body conforms to the resilient material 94. The foam cuff 72 conforms more to the peaks 24 of the laryngeal rim 20 than the peaks 24 conform to the foam cuff 72. This conformity decreases the amount of pressure applied to the peaks 24 and reduces the likelihood of injury to the airway tissues. Furthermore, this conformity allows the foam cuff 72 to more completely fill the valleys 26 of the laryngeal rim 20 and the irregularly contoured U-shaped channels 28 to form an effective seal.

In cases where the foam cuff 72 cannot completely expand to fill in the valleys 26 of the laryngeal rim 20 and U-shaped channels 28, positive pressure introduced by use of a syringe or like positive pressure-creating device can be applied through the port 98 to further expand the resilient material 94 and thus the foam cuff 72. This increased expansion allows the foam cuff 72 to more completely fill the valleys 26 and irregularly contoured U-shaped channels 28 and also reduces the height of the peaks 24 because of the increased pressure placed on the peaks 24 by the resilient material 94.

FIG. 12 shows a conventional laryngeal mask 112 including an inflatable ring cuff 114 in a deflated position. Unlike the foam cuff 72 according to the present invention, the inflatable ring cuff 114 requires positive pressure from a positive pressure-creating device to inflate because ambient air pressure is not sufficient to inflate the inflatable ring cuff 114. The inflation process consumes valuable medical personnel time that could be dedicated to other functions beneficial to the patient. Therefore, the foam cuff 72 according to the present invention saves medical personnel time over the inflatable ring cuff 114 because it is unnecessary to manually re-inflate the foam cuff 72 to its ambient position.

The inflatable ring cuff 114 includes a front end 115 and an inflatable ring cuff tip 116 positioned to lie the front end 115. The deflated inflatable ring cuff tip 116 has a tendency to "hinge" back if force is applied to it.

Figure 13:
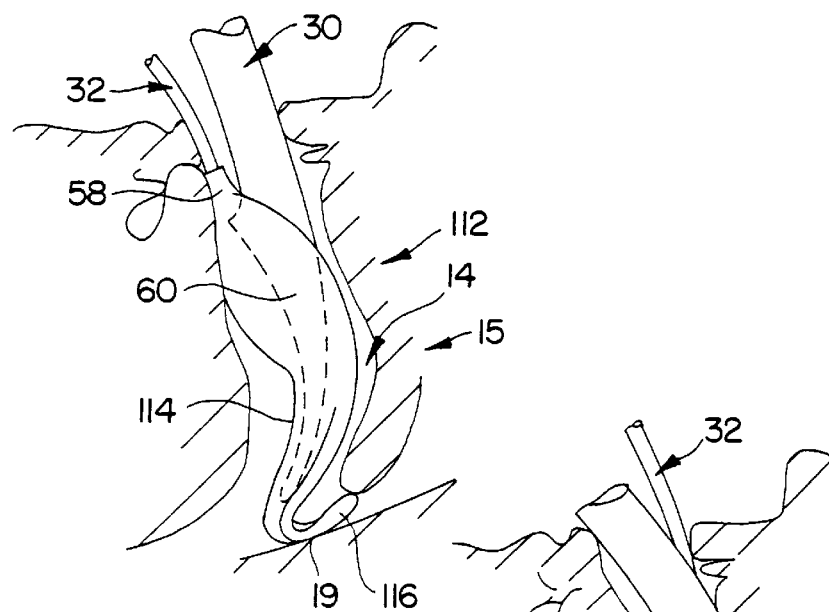
FIG. 13 is a sectional view of a patient showing a conventional laryngeal mask airway of FIG. 12 inserted into the patient's airway, the conventional inflatable ring cuff being in a deflated position and including a deflated ring cuff tip, and the deflated ring cuff tip making contact with a posterior pharyngeal wall of the patient causing the deflated ring cuff tip to fold back.
Figure 14:
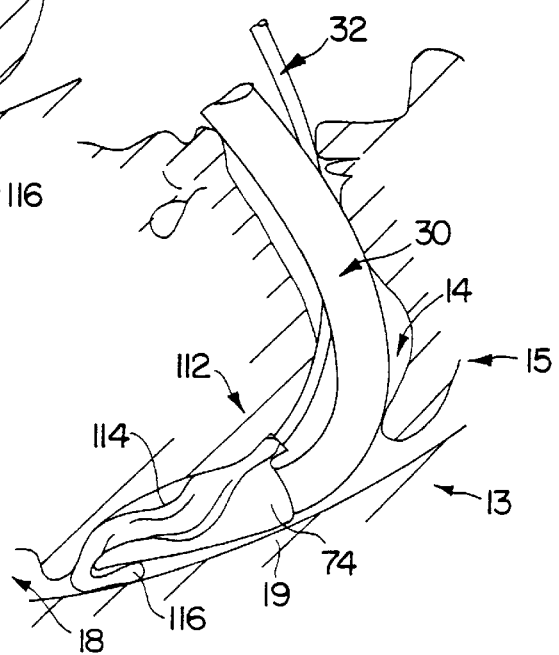
FIG. 14 is a cross sectional view of a patient showing the conventional laryngeal mask airway of FIG. 12 inserted deeper into the patient's airway and the deflated inflatable ring cuff tip folded back, thus precluding the possibility of creating a seal with the patient's laryngeal rim.
Figure 17:
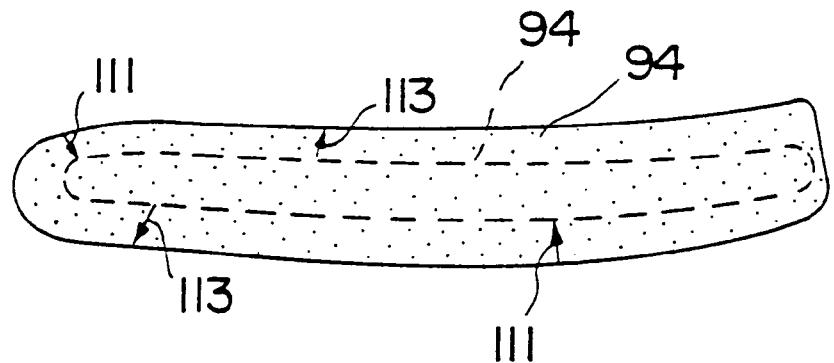
FIG. 17 is a sectional view taken along line 17—17 of FIG. 2 of the resilient material of the present invention.

FIG. 13 shows the inflatable ring cuff tip 116 folding back because the inflatable ring cuff tip 116 has struck the posterior pharyngeal wall 19 of the patient's airway 14 during insertion. As shown in FIG. 14, when completely inserted, the inflatable ring cuff tip 116 is completely folded back and has failed to form an acceptable seal over the laryngeal opening 18. Therefore, the conventional laryngeal mask 112 must be removed, re-prepared for insertion, and reinserted into the patient's airway 14. Medical personnel attempting to insert the conventional laryngeal mask 112 not only consume valuable time re-inserting the conventional laryngeal mask 112, but also must pay extra attention to ensure the inflatable ring cuff tip 116 does not fold back during insertion.

As shown in FIG. 15, the foam cuff 72 includes a foam cuff tip 118 located at the front end 76 and having a foam cuff tip length 120. The foam cuff tip length 120 is measured along the longitudinal axis 64 from the distal end 70 of the back plate 60 to the front end 76 of the foam cuff 72. Likewise, the inflatable ring cuff tip 116 of the conventional laryngeal mask 112, shown in FIG. 12, has an inflatable ring cuff tip length 122 and a front end 115. The conventional laryngeal mask 112 includes a back plate 117 having a distal end 119 and a proximal end 121 and a longitudinal axis 123 extending through the distal end 119 and proximal end 121. The inflatable ring cuff tip length 122 is also measured along the longitudinal axis 123 from the distal end 119 of back plate 117 to the front end 115.

As foam cuff 72 deflates, the foam cuff tip length 120 decreases because the resilient material 94 recedes inward in direction 111 toward the back plate 60 as shown, for example, in FIG. 15. However, as conventional inflatable ring cuff 114 deflates, the inflatable ring cuff tip length 122 does not experience a similar decrease. Therefore, when both the foam cuff 72 and the inflatable ring cuff 114 are in their deflated positions, the inflatable ring cuff tip length 122 is greater than the foam cuff tip length 120.

The resilient material 94 also becomes more rigid as it deflates. The pliable structure of the resilient material 94 becomes more rigid as resilient material 94 deflates and the size of the air pockets within the resilient material 94 decreases. This increase in the rigidity of the resilient material 94 also increases the rigidity of the foam cuff tip 118. This increased rigidity of the foam cuff tip 118, decreases the tendency of the foam cuff tip 118 to hinge back compared to the inflatable ring cuff tip 116 of the conventional inflatable ring cuff 114. Therefore, the foam cuff tip 118 is less likely to fold back than the conventional inflatable ring cuff tip 116 of the conventional laryngeal mask 112 because of the higher rigidity of the foam cuff tip 118 and the shorter deflated foam cup tip length 120.

The foam cuff 72 has a foam cuff width 124, a first edge 126, and a second edge 128 spaced apart from the first edge 126 along the latitudinal axis 66. The foam cuff width 124 is measured along the latitudinal axis 66 from the first edge 126 to the second edge 128 as shown in FIG. 15. Likewise, the inflatable ring cuff 114 of the conventional laryngeal mask 112, as shown in FIG. 12, has a latitudinal axis 129, an inflatable ring cuff width 130, a first edge 131, and a second edge 133 spaced apart from the first edge 131 along the latitudinal axis 129. The inflatable ring cuff width 130 is also measured along the latitudinal axis 129 from the first edge 131 to the second edge 133.

Because the foam cuff 72 decreases in volume and recedes inward in direction 111 toward the back plate 60 during deflation, the foam cuff width 124 decreases during deflation. The inflatable ring cuff width 130 of the conventional laryngeal mask 112 does not decrease in width as much as foam cuff 72. Therefore, during insertion, the foam cuff 72 is easier to insert into the patient's airway 14 than the inflatable ring cuff 114 of the conventional laryngeal mask 112 because of the decrease in the foam cuff width 124.

Figure 18:
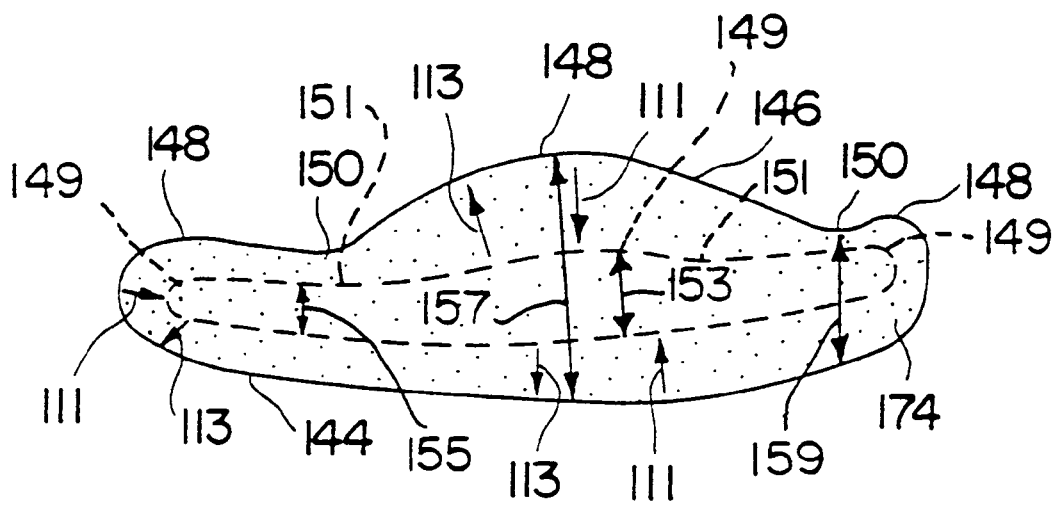
FIG. 18 is a sectional view of another preferred embodiment of the present invention, similar to FIG. 17, showing the resilient material contoured to substantially match the configuration of the laryngeal rim and U-shaped channels.

In another preferred embodiment of the present invention, shown in FIG. 18, a resilient material 174 having a contoured surface is provided that substantially matches the contour of the laryngeal rim 20 and the irregularly contoured U-shaped channels 28. The resilient material 174 includes a top side 144 and a sealing side 146. The sealing side 146 is formed to have crests 148 and canyons 150 due to the contoured shape of resilient material 174. The crests 148 of the contoured resilient material 174 are substantially aligned to custom fit into the valleys 26 of the laryngeal rim 20. As shown in FIG. 18, the resilient material 174 is preformed with deflated crests 149 and deflated canyons 151. The deflated crests 149 include a deflated crest depth 153 and the deflated canyons 151 include a deflated canyon depth 155 that is less than the deflated crest depth 153. As shown in FIG. 18, when the resilient material 94 expands in direction 113, the inflated crests 148 include an inflated crest depth 157 and the inflated canyons 150 include an inflated canyon depth 159 that is less than the inflated crest depth 157. The canyons 150 of the contoured foam cuff 172 are substantially aligned to engulf the peaks 24 of the laryngeal rim 20. Furthermore, the resilient material 174 is also contoured to fill the irregularly contoured U-shaped channels 28. Therefore, less expansion of the resilient material 174 is necessary to fill in the valleys 26 of the laryngeal rim 20 and U-shaped channels 28 and less pressure is placed on the peaks 24. This will allow for a better seal and less tissue-damaging pressure. The alignment of the crests 148 and canyons 150 can be custom formed for individual patients 12 or for an average patient to allow for mass production.

Furthermore, when inflating pressure is applied to the resilient material 174, the crests 148 will expand more than the canyons 150 because the crests 148 have more volume than the canyons 150 as shown, for example, in FIG. 18 (deflated position in phantom). Because of the expansive nature of the resilient material 94, the higher volume crests 148 will expand more than the lower volume canyons 150. This will allow the crests 148 to fill more of the valleys 26 without the canyons 150 applying excessive pressure on the peaks 24 of the laryngeal rim 20.

Additional objects, features, and advantages of the invention will become apparent to those skilled in the art upon consideration of the following detailed description of preferred embodiments exemplifying the best mode of carrying out the invention as presently perceived.

I claim:

1. A laryngeal mask airway for use in patients having a larynx, a patient's larynx including a laryngeal opening and a laryngeal rim surrounding the laryngeal opening, and a patient's laryngeal rim including peaks and valleys, the laryngeal mask airway comprising an air tube having a proximal end and a mask end spaced apart from the proximal end, and a laryngeal mask being attached to the mask end of the air tube, the laryngeal mask including a foam cuff, the foam cuff being formed to include an interior region and including a resilient material positioned to lie within the interior region, the resilient material being configured to expand and deflate between a deflated position and an expanded position to substantially seal over a patient's laryngeal opening, the foam cuff further including a sealing side that is adapted to engage a patient's laryngeal rim, and the resilient material being formed to include crests and canyons on the sealing side that substantially align with a patient's peaks and valleys in the patient's laryngeal rim.

2. The laryngeal mask airway of claim 1, wherein the resilient material is formed to include a plurality of interconnected air pockets and the resilient material uniformly deflates under deflating pressure and uniformly expands under inflating pressure.

3. The laryngeal mask airway of claim 1, wherein the rigidity of the resilient material increases as resilient material deflates.

4. The laryngeal mask airway of claim 3, wherein the foam cuff includes a front end, a back end spaced apart from the front end, and a foam cuff tip positioned at the front end, and the foam cuff tip includes a rigidity that increases as the foam cuff deflates.

5. The laryngeal mask airway of claim 1, wherein the resilient material includes a volume that is pressure sensitive and the volume changes as pressure is applied to the resilient material.

6. The laryngeal mask airway of claim 1, wherein the laryngeal mask further includes a back plate having an outer rim, the foam cuff is attached to the outer rim, the back plate further includes a longitudinal axis, a proximal end, and a distal end spaced apart from the proximal end along the longitudinal axis, the foam cuff further includes a front end, a back end spaced apart from the front end along the longitudinal axis, and a foam cuff tip positioned at the front end, the foam cuff tip includes a foam cuff tip length measured along the longitudinal axis from the distal end of the back plate to the front end of the foam cuff, and the foam cuff tip length decreases as the resilient material deflates.

7. The laryngeal mask airway of claim 1, wherein the laryngeal mask further includes a back plate having an outer rim, the foam cuff is attached to the outer rim, the back plate further includes a latitudinal axis, the foam cuff further includes a first edge, a second edge spaced apart from the first edge along the latitudinal axis, and a foam cuff width measured along the latitudinal axis from the first edge of the foam cuff to the second edge of the foam cuff, and the foam cuff width decreases as the resilient material deflates.

8. The foam cuff of claim 1, wherein the pliable sheath is formed to include a port to form a deflation air passage from the resilient material through the pliable sheath.

9. The laryngeal mask airway of claim 1, wherein the resilient material is preformed to include crests and canyons.

10. The laryngeal mask airway of claim 9, wherein the crests include a deflated crest depth in the deflated position and the canyons include a deflated canyon depth in the deflated position that is less than the deflated crest depth.

11. The laryngeal mask airway of claim 1, wherein the crests include a crest depth and the canyons include a canyon depth that is less than the crest depth.

12. A laryngeal mask airway for use in patients having a larynx, a patient's larynx including a laryngeal opening, U-shaped channels, and a laryngeal rim surrounding the laryngeal opening, and a patient's laryngeal rim including peaks and valleys, the laryngeal mask airway comprising an air tube having a proximal end and a mask end spaced apart from the proximal end, and a laryngeal mask being attached to the mask end of the air tube, the laryngeal mask including a foam cuff, the foam cuff being formed to include an interior region and including a resilient material positioned to lie within the interior region, the resilient material being configured to expand and deflate between a deflated position and an expanded position to substantially seal over a patient's laryngeal opening, and the foam cuff including means for increasing resistance against laryngeal mask motion in a direction perpendicular to a patients' valleys' and U-shaped channels' depth, wherein the foam cuff further includes a sealing side that is adapted to engage a patient's laryngeal rim and the means for increasing resistance include the resilient material being formed to include crests and canyons on the sealing side that substantially align with a patient's peaks and valleys in such a patient's laryngeal rim.

13. The laryngeal mask airway of claim 1, wherein the resilient material is preformed to include crests and canyons.

14. The laryngeal mask airway of claim 30, wherein the crests include a deflated crest depth in the deflated position and the canyons include a deflated canyon depth in the deflated position that is less than the deflated crest depth.

15. The laryngeal mask airway of claim 1, wherein the crests include a crest depth and the canyons include a canyon depth that is less than the crest depth.

16. The laryngeal mask airway of claim 1, wherein the resilient material is formed to include a plurality of interconnected air pockets and the resilient material uniformly deflates under deflating pressure and uniformly expands under inflating pressure.

17. The laryngeal mask airway of claim 12, wherein the rigidity of the resilient material increases as resilient material deflates.

18. The laryngeal mask airway of claim 12, wherein the resilient material includes a volume that is pressure sensitive and the volume changes as pressure is applied to the resilient material.

19. The laryngeal mask airway of claim 12, wherein the laryngeal mask further includes a back plate having an outer rim, the foam cuff is attached to the outer rim, the back plate further includes a longitudinal axis, a proximal end, and a distal end spaced apart from the proximal end along the longitudinal axis, the foam cuff further includes a front end, a back end spaced apart from the front end along the longitudinal axis, and a foam cuff tip positioned at the front end, the foam cuff tip includes a foam cuff tip length measured along the longitudinal axis from the distal end of the back plate to the front end of the foam cuff, and the foam cuff tip length decreases as the resilient material deflates.

20. The laryngeal mask airway of claim 12, wherein the laryngeal mask further includes a back plate having an outer rim, the foam cuff is attached to the outer rim, the back plate further includes a latitudinal axis, the foam cuff further includes a first edge, a second edge spaced apart from the first edge along the latitudinal axis, and a foam cuff width measured along the latitudinal axis from the first edge of the foam cuff to the second edge of the foam cuff, and the foam cuff width decreases as the resilient material deflates.

21. The foam cuff of claim 12, wherein the pliable sheath is formed to include a port to form a deflation air passage from the resilient material through the pliable sheath.

22. A laryngeal mask airway for use in patients having a larynx, a patient's larynx including a laryngeal opening, U-shaped channels, and a laryngeal rim surrounding the laryngeal opening, and a patient's laryngeal rim including peaks and valleys, the laryngeal mask airway comprising an air tube having a proximal end and a mask end spaced apart from the proximal end, and a laryngeal mask being attached to the mask end of the air tube, the laryngeal mask including a foam cuff, the foam cuff including a foam cuff tip, an interior region, and means for increasing the rigidity of the foam cuff tip to decrease the tendency of the foam cuff tip to fold when the laryngeal mask is inserted into a patient's airway.

23. The laryngeal mask of claim 22, wherein the laryngeal mask further includes a back plate having an outer rim, the foam cuff is attached to the outer rim, the back plate further includes a longitudinal axis, a proximal end, and a distal end spaced apart from the proximal end along the longitudinal axis, the foam cuff further includes a front end and a back end spaced apart from the front end along the longitudinal axis, and the foam cuff tip is positioned at the front end of the foam cuff.

24. A method of inserting a laryngeal mask airway into a patient's airway and using the laryngeal mask airway to substantially seal over a patient's larynx, the method comprising the steps of providing a laryngeal mask airway and a pressure-creating device, the laryngeal mask airway including an air tube and a laryngeal mask coupled to the air tube, the laryngeal mask including a foam cuff having an interior region, a foam cuff tip having a foam cuff tip length, and means for increasing the rigidity of the foam cuff tip to decrease the tendency of the foam cuff tip to fold when the laryngeal mask is inserted into a patient's airway, reducing the foam cup tip length of the foam cuff by using the pressure-creating device to lower the pressure within the interior region of the foam cuff, inserting the foam cuff into a patient's airway such that the foam cuff tip is the first portion of the foam cuff inserted in a patient's airway, positioning the foam cuff over a patient's laryngeal opening, and increasing the pressure within the interior region of the foam cuff which will increase the foam cup tip length.

* * * * *